United States Patent
Joshi et al.

(10) Patent No.: US 9,771,364 B2
(45) Date of Patent: *Sep. 26, 2017

(54) PROCESS FOR PREPARATION OF (2S,5R)-6-SULPHOOXY-7-OXO-2-[((3R)-PIPERIDINE-3-CARBONYL)-HYDRAZINOCARBONYL]-1,6-DIAZA-BICYCLO[3.2.1] OCTANE

(71) Applicant: WOCKHARDT LIMITED, Aurangabad (IN)

(72) Inventors: Sanjeev Joshi, Aurangabad (IN); Sunil Bhaginath Jadhav, Ahmednagar (IN); Vipul Rane, Aurangabad (IN); Satish Bhawsar, Aurangabad (IN); Prasad Keshav Deshpande, Aurangabad (IN); Ravindra Dattatraya Yeole, Aurangabad (IN); Mahesh Vithalbhai Patel, Maharashtra (IN)

(73) Assignee: WOCKHARDT LIMITED, Chikalthana, Aurangabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/108,296

(22) PCT Filed: Dec. 29, 2014

(86) PCT No.: PCT/IB2014/067377
§ 371 (c)(1),
(2) Date: Jun. 25, 2016

(87) PCT Pub. No.: WO2015/110885
PCT Pub. Date: Jul. 30, 2015

(65) Prior Publication Data
US 2016/0340359 A1    Nov. 24, 2016

(30) Foreign Application Priority Data

Jan. 21, 2014 (IN) ............................ 195/MUM/2014

(51) Int. Cl.
*C07D 471/08* (2006.01)

(52) U.S. Cl.
CPC ........ *C07D 471/08* (2013.01); *C07B 2200/13* (2013.01)

(58) Field of Classification Search
CPC .................................................. C07D 471/08
See application file for complete search history.

(56) References Cited

U.S. PATENT DOCUMENTS

2013/0225554 A1* 8/2013 Maiti .................. C07D 519/00
514/210.21

FOREIGN PATENT DOCUMENTS

WO    WO2013030733 A1    3/2013
WO    WO2014135931 A1    9/2014

OTHER PUBLICATIONS

Caira M R: "Crystalline Polymorphism of Organic Compounds", Topics in Current Chemistry,Springer, Berlin, DE, vol. 198, Jan. 1, 1998 (Jan. 1, 1998), pp. 163-208, Abstract.

Valeur et al: "Amide bond formation: beyond the myth of coupling reagents", Chemical Society Reviews, vol. 38, No. 2, Jan. 1, 2009 (Jan. 1, 2009), p. 606, XP55025820, ISSN: 0306-0012, DOI: 10.1039/b701677h, Abstract.

Peterson et al., Iterative High-Throughput Polymorphism Studies on Acetaminophen and an Experimentally Derived Structure for Form IIIAm. Chem. Soc., 124, 10958-10959, 10958 (2002).

Morissette et al., High-throughput crystallization: Polymorphs, salts, co-crystals and solvates of pharmaceutical solidsAdvanced Drug Delivery Reviews, 56, 275-300, 296 (2004).

Buar et al., Disappearing Polymorphs Revisited (pp. 6972-6993)Angew. Chem. Int. Ed., 54, 6972-6993 (2015).

* cited by examiner

*Primary Examiner* — Bruck Kifle
(74) *Attorney, Agent, or Firm* — Bio Intellectual Property Services LLC (Bio IPS); O. (Sam) Zaghmout

(57) ABSTRACT

A process for preparation of a compound of Formula (I) is disclosed.

(I)

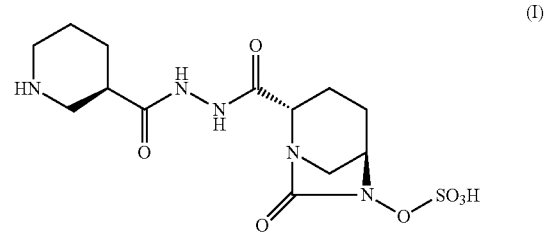

11 Claims, 2 Drawing Sheets

PROCESS FOR PREPARATION OF (2S,5R)-6-SULPHOOXY-7-OXO-2-[((3R)-PIPERIDINE-3-CARBONYL)-HYDRAZINOCARBONYL]-1,6-DIAZA-BICYCLO[3.2.1] OCTANE

RELATED PATENT APPLICATIONS

This application claims priority to Indian Patent Application No. 195/MUM/2014 filed on Jan. 21, 2014, the disclosures of which are incorporated herein by reference in its entirety as if fully rewritten herein.

FIELD OF THE INVENTION

The invention relates to a process for preparation of (2S,5R)-6-sulphooxy-7-oxo-2-[((3R)-piperidine-3-carbonyl)-hydrazinocarbonyl]-1,6-diaza-bicyclo[3.2.1]octane.

BACKGROUND OF INVENTION

A compound of Formula (I), chemically known as (2S,5R)-6-sulphooxy-7-oxo-2-[((3R)-piperidine-3-carbonyl)-hydrazinocarbonyl]-1,6-diaza-bicyclo[3.2.1]octane has antibacterial properties and is disclosed in PCT International Patent Application No. PCT/IB2012/054290.

Formula (I)

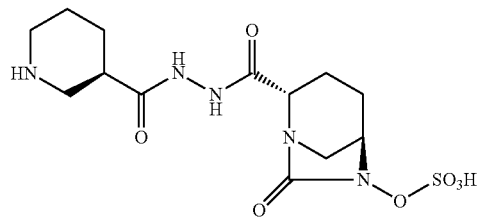

SUMMARY OF THE INVENTION

In one general aspect, there is provided a process for preparation of a compound of Formula (I), comprising:

Formula (I)

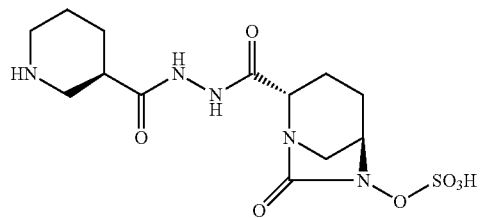

(a) hydrogenolysis of a compound of Formula (II) to obtain a compound of Formula (III);

Formula (II)

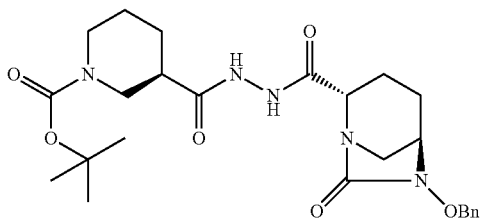

Formula (III)

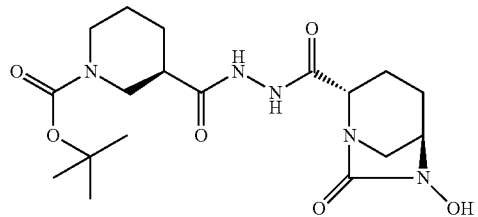

(b) converting a compound of Formula (III) to a compound of Formula (IV);

Formula (IV)

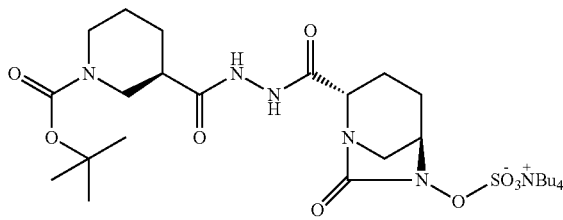

(c) purifying a compound of Formula (IV) using a siliceous material; and (d) converting a compound of Formula (IV) obtained in step (c) to a compound of Formula (I).

In one general aspect, there is provided a compound of Formula (I) having purity of more than about 98% as determined by HPLC.

In another general aspect, there is provided a compound of Formula (I) in amorphous or crystalline forms.

In another aspect, there are provided processes for preparation of a compound of Formula (I) in amorphous or crystalline forms.

The details of one or more embodiments of the inventions are set forth in the description below. Other features, objects and advantages of the inventions will be apparent from the following description including claims.

DETAILED DESCRIPTION OF THE INVENTION

Figure 1:
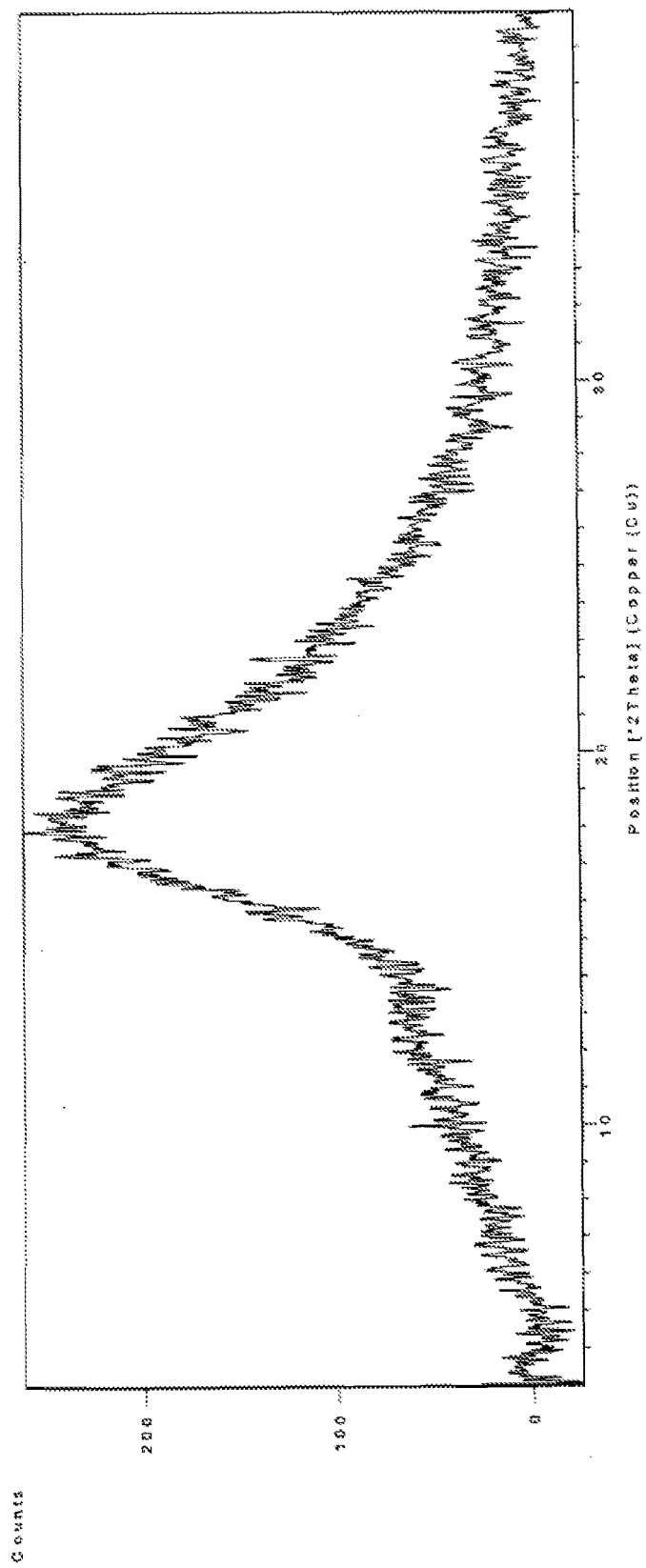
FIG. 1—represents a X-ray powder diffraction pattern of the amorphous form of (2S, 5R)-7-oxo-6-sulphooxy-2-[((3R)-piperidine-3-carbonyl)-hydrazinocarbonyl]-1,6-diaza-bicyclo[3.2.1]octane.

Reference will now be made to the exemplary embodiments, and specific language will be used herein to describe the same. It should nevertheless be understood that no limitation of the scope of the invention is thereby intended. Alterations and further modifications of the inventive features illustrated herein, which would occur to one skilled in the relevant art and having possession of this disclosure, are to be considered within the scope of the invention. It must be noted that, as used in this specification and the appended claims, the singular forms "a", "an", and "the" include plural referents unless the content clearly dictates otherwise. All references including patents, patent applications, and literature cited in the specification are expressly incorporated herein by reference in their entirety.

The term "OBn" as used herein refers to benzyloxy.

The term "Boc" as used herein refers to tert-butyloxycarbonyl.

In one general aspect, there is provided a process for preparation of a compound of Formula (I), comprising:

Formula (I)

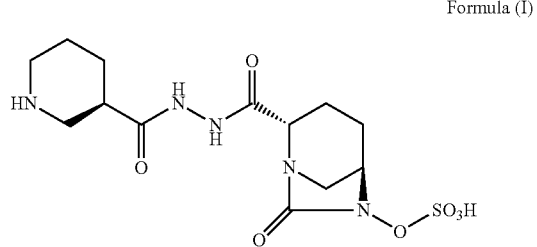 [SMILES: O=C(NNC(=O)[C@@H]1CC[C@@H]2CN1C(=O)N2OS(=O)(=O)O)[C@@H]1CCCNC1]

(a) hydrogenolysis of a compound of Formula (II) to obtain a compound of Formula (III);

Formula (II)

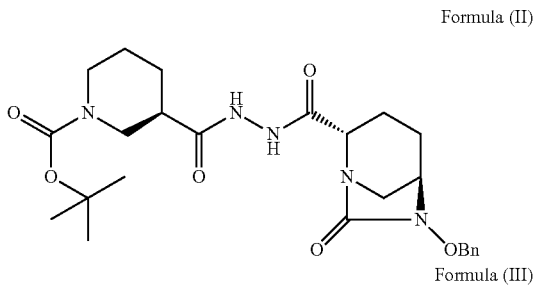

Formula (III)

(b) converting a compound of Formula (III) to a compound of Formula (IV);

Formula (IV)

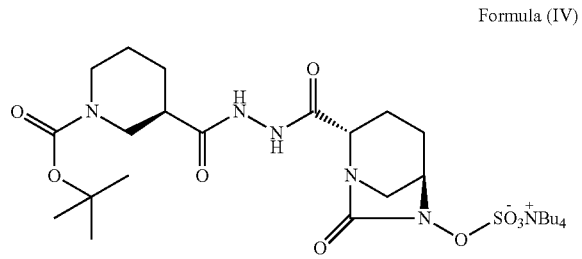

(c) purifying a compound of Formula (IV) using a siliceous material; and (d) converting a compound of Formula (IV) obtained in step (c) to a compound of Formula (I).

The compound of Formula (I) is synthesized starting from a compound of Formula (II) as disclosed in Scheme 1. The compound of Formula (II) is treated with a suitable hydrogenolysis agent to provide a compound of Formula (III). In some embodiments, hydrogenolysis of a compound of Formula (II) to obtain a compound of Formula (III) is carried out in presence of a transition metal catalyst and a hydrogen source. In some other embodiments, the transition metal catalyst is palladium on carbon, and hydrogen source is hydrogen gas. In some other embodiments, the hydrogenolysis reaction is carried out in presence of suitable solvent or mixture of solvents. In some embodiments, the hydrogenolysis of a compound of Formula (II) to obtain a compound of Formula (III) is carried out using 10% palladium on carbon catalyst, in presence of hydrogen gas and in methanol as a solvent.

The compound of Formula (IV) is obtained by sulfonating a compound of Formula (III). The sulfonation reaction can be carried out in presence of a suitable sulfonating agent in presence of a suitable solvent. In some embodiments, the sulfonation of a compound of Formula (III) is carried out by reacting it with pyridine-sulfur trioxide complex, in dichloromethane as solvent, followed by treatment with tetrabutyl ammonium acetate to obtain a compound of Formula (IV).

The compound of Formula (IV) is purified before converting to a compound of Formula (I). In some embodiments, a compound of Formula (IV) is purified by treatment with one or more siliceous material. In some embodiments, a compound of Formula (IV) is treated with silica gel to enhance the purity of a compound of Formula (IV) to more than about 98% as determined by HPLC.

The purified compound of Formula (IV) is converted to a compound of Formula (I) in presence of a suitable deprotecting reagent. In some embodiments, purified compound of Formula (IV) is converted to a compound of Formula (I) by reacting a compound of Formula (IV) with trifluoroacetic acid in suitable solvent such as dichloromethane.

The compound of Formula (IV), purified by using siliceous material, is converted to a compound of Formula (I) of enhanced purity. In some other embodiments, purified compound of Formula (IV) is converted to a compound of Formula (I) by treating with trifluoroacetic acid. In some other embodiments, compound of Formula (IV), purified by using silica gel, is converted to a compound of Formula (I). In some embodiments, the purity of a compound of Formula (I), obtained from a purified compound of Formula (IV), is more than about 98% as determined by HPLC.

In some embodiments, there is provided a compound of Formula (I) having a purity of more than about 98% as determined by HPLC. In some other embodiments, there is provided a compound of Formula (I) having a melting point of 278° C. as determined by DSC.

In some other embodiments, the compound of Formula (I) is prepared using a process described in Scheme I. In some embodiments, there is provided a process for preparation of compound of Formula (I) having purity of more than about 98% as determined by HPLC.

In some embodiments, there is provided a compound of Formula (I) in amorphous form.

In some embodiments, there is provided a compound of Formula (I) in amorphous form as shown in FIG. 1.

In some embodiments, there is provided a process for preparation of a compound of Formula (I) in amorphous form, comprising: (a) dissolving a compound of Formula (IV) in a suitable solvent to obtain a clear solution; (b)

treating the solution obtained in step (a) with trifluoroacetic acid (c) removing solvent from the reaction mass to obtain a residue; (d) adding the residue obtained in step (c) to diethyl ether under stirring; (e) decanting the diethylether and washing the residue obtained with acetonitrile; (f) repeating the step (e) with dichloromethane; and (g) isolating a compound of Formula (I) in amorphous form.

group consisting of 10.31 (±0.2), 12.56 (±0.2), 13.84 (±0.2), 15.65 (±0.2), 18.19 (±0.2), 18.51 (±0.2), 20.38 (±0.2) and 24.30 (±0.2) degrees 2 theta.

In some embodiments, there is provided a pharmaceutical composition comprising a compound of Formula (I) according to invention. In some embodiments, there is provided a compound of Formula (I) in crystalline or amorphous form.

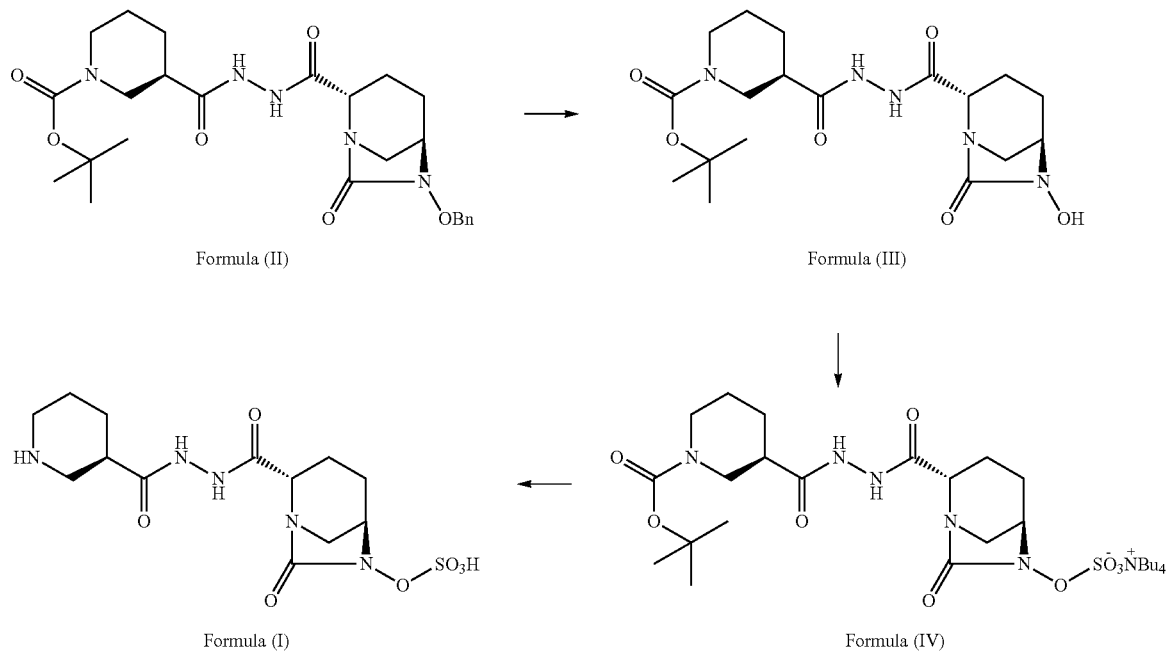

Scheme 1

In some other embodiments, there is provided a compound of Formula (I) in crystalline form.

Figure 2:
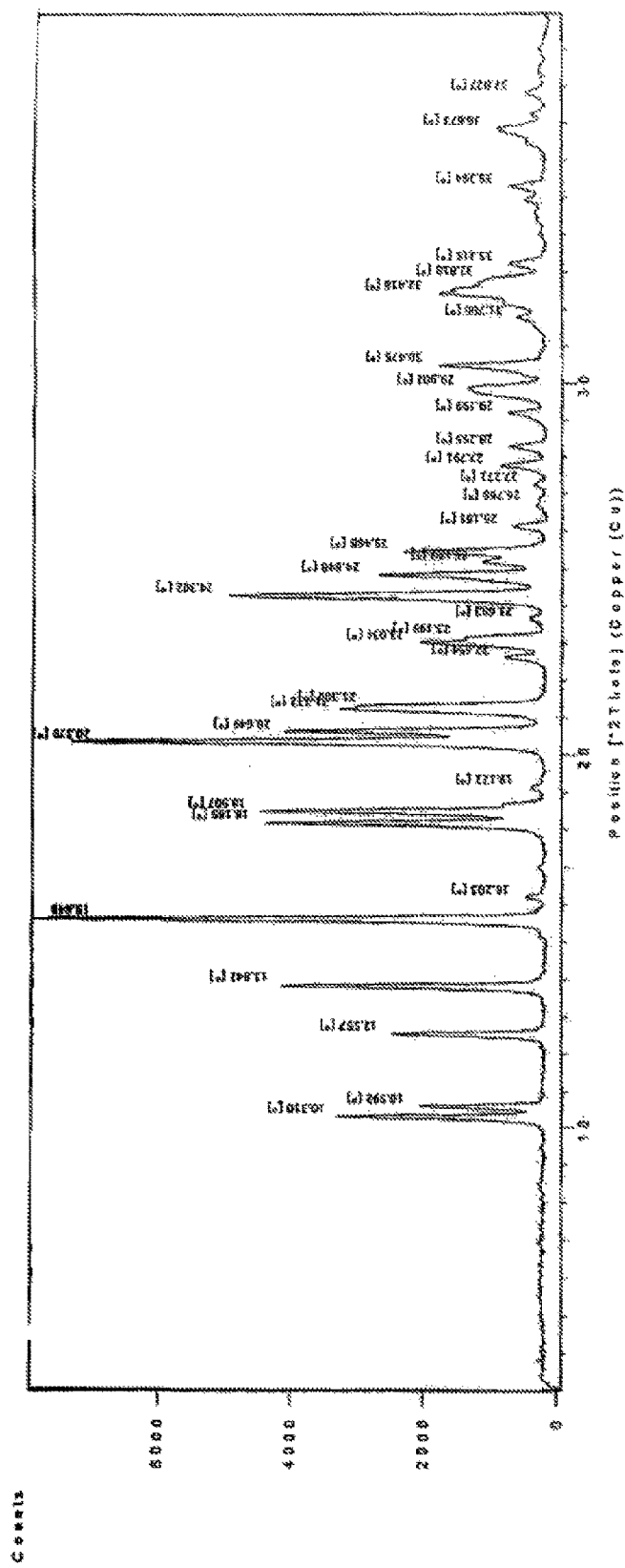
FIG. 2—represents a X-ray powder diffraction pattern of the crystalline form of (2S, 5R)-7-oxo-6-sulphooxy-2-[((3R)-piperidine-3-carbonyl)-hydrazinocarbonyl]-1,6-diaza-bicyclo[3.2.1]octane.

In some other embodiments, there is provided a compound of Formula (I) in crystalline form having XRD as shown in FIG. 2.

In some embodiments, there is provided a process for preparation of a compound of Formula (I) in crystalline form, which comprises: (a) dissolving a compound of Formula (I) in water to obtain a homogeneous mixture; (b) adding isopropyl alcohol to the homogeneous mixture obtained in step (a) under stirring; and (c) isolating a compound of Formula (I) in crystalline form.

In some embodiments, a compound of Formula (I) is obtained in crystalline form by dissolving compound of Formula (I) in one or more suitable solvent such as mixture of water and isopropyl alcohol. In some other embodiments, a compound of Formula (I) is obtained in crystalline form by dissolving compound of Formula (I) in mixture of water and isopropyl alcohol (1:7).

In some embodiments, a compound of Formula (I) is obtained in crystalline form, having an X-ray powder diffraction pattern comprising a peak selected from the group consisting of 10.31 (±0.2), 10.59 (±0.2), 12.56 (±0.2), 13.84 (±0.2), 15.65 (±0.2), 18.19 (±0.2), 18.51 (±0.2), 20.38 (±0.2), 20.65 (±0.2), 24.30 (±0.2), 24.85 (±0.2) and 25.47 (±0.2) degrees 2 theta.

In some other embodiments, a compound of Formula (I) is obtained in crystalline form, having an X-ray powder diffraction pattern comprising a peak selected from the In some embodiments, there is provided a pharmaceutical composition comprising a compound of Formula (I) having purity of more than about 98% as determined by HPLC. The pharmaceutical composition comprising a compound of Formula (I) according to invention may include one or more pharmaceutically acceptable inactive ingredients.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Synthesis of (2S, 5R)-7-oxo-6-sulphooxy-2-[((3R)-piperidine-3-carbonyl)-hydrazinocarbonyl]-1,6-diaza-bicyclo[3.2.1]octane (I)

Step-1: Preparation of (2S, 5R)-6-hydroxy-7-oxo-2-[((3R)—N-Boc-piperidine-3-carbonyl)-hydrazinocarbonyl]-1,6-diaza-bicyclo[3.2.1]octane (III)

(2S, 5R)-6-benzyloxy-7-oxo-2-[((3R)—N-Boc-piperidine-3-carbonyl)-hydrazino-carbonyl]-1,6-diazabicyclo[3.2.1]octane (II) (130 g, 0.259 mol) was dissolved in methanol (1040 ml) to obtain a clear solution. To this solution, was added 10% palladium on carbon (13 g, 0.26 mol). The suspension was stirred under 230-250 psi hydrogen atmosphere at temperature of about 30° C. for about 2 hour. The catalyst was filtered over celite bed and catalyst containing bed was washed with additional methanol (400 ml). The methanolic solution was re-filtered through fresh celite bed and washed with methanol (100 ml). The filtrate was concentrated under vacuum at temperature of about 30° C. to obtain the off white solid as product. The so obtained solid was stirred with cyclohexane (750 ml). The solid was then filtered and washed with cyclohexane (320 ml) and dried under suction to obtain 107 g of (2S, 5R)-6-hydroxy-7-oxo-2-[((3R)—N-Boc-piperidine-3-carbonyl)-hydrazinocarbonyl]-1,6-diaza-bicyclo[3.2.1]octane (III).

Analysis:
Mass: 412.4 (M+1); for Molecular Formula of $C_{18}H_{29}N_5O_6$ and Molecular Weight of 411.5; and
Purity as determined by HPLC: 98.02%.

Step-2: Preparation of tetrabutylammonium salt of (2S, 5R)-6-sulfooxy-7-oxo-2-[((3R)—N-Boc-piperidine-3-carbonyl)-hydrazinocarbonyl]-1,6-diaza-bicyclo[3.2.1] octane (IV)

A solution of (2S, 5R)-6-hydroxy-7-oxo-2-[((3R)—N-Boc-piperidine-3-carbonyl)-hydrazinocarbonyl]-1,6-diaza-bicyclo[3.2.1]octane (III) (106 g, 0.26 mol) in dichloromethane was charged with triethyl amine (110 ml, 0.78 mol) under stirring. To this clear solution was added pyridine sulfur trioxide complex (82.5 g, 0.53 mol) under nitrogen atmosphere and stirred at temperature of about 30° C. for about 2 hour. The reaction mixture was diluted with 0.5 N aqueous potassium dihydrogen phosphate solution (2100 ml) followed by ethyl acetate (2100 ml). The turbid solution was stirred for 15 minute and then the layers were separated. The aqueous layer was washed with dichloromethane (530 ml) and then with ethyl acetate (1060 ml). Tetrabutyl ammonium sulfate (79 g, 0.23 mol) was added to the separated aqueous layer and stirred for 12 hour. The extraction of the product was done using dichloromethane as solvent (1150 ml×2). The organic layer was dried over sodium sulfate and then evaporated under vacuum at temperature below 40° C. to furnish 108 g of tetrabutylammonium salt of (2S, 5R)-6-sulfooxy-7-oxo-2-[((3R)—N-Boc-piperidine-3-carbonyl)-hydrazinocarbonyl]-1,6-diaza-bicyclo [3.2.1]octane (IV).

Analysis:
Mass: 490.3 (M−1) as free sulfonic acid; for Molecular Formula of $C_{18}H_{28}N_5O_9S.N(C_4H_9)_4$ and Molecular weight of 733.0; and Purity as determined by HPLC: 86.50%.

Step-3: Preparation of (2S, 5R)-7-oxo-6-sulphooxy-2-[((3R)-piperidine-3-carbonyl)-hydrazinocarbonyl]-1,6-diaza-bicyclo[3.2.1]octane (I)

Tetrabutylammonium salt of (2S, 5R)-6-sulfooxy-7-oxo-2-[((3R)—N-Boc-piperidine-3-carbonyl)-hydrazinocarbonyl]-1,6-diaza-bicyclo[3.2.1]octane (IV) (88 g, 0.12 mol) was dissolved in dichloromethane (225 ml). The reaction mass was cooled to about −10° C. and to this trifluoroacetic acid (225 ml) was added slowly. The reaction mixture was stirred for 1 hour at temperature of about −10° C. The solvent was removed under high vacuum at about 30° C. The residue (280 g) was stirred with diethyl ether (1320 ml) for 1 hour. The precipitated solid was filtered and the cake was washed with fresh diethyl ether (440 ml). This process was repeated with fresh diethyl ether (1320 ml+440 ml). The obtained white solid was dried at temperature of about 30° C. and suspended in acetone (1320 ml). The pH of the suspension was adjusted to 6.5-7.0 using 10% solution of sodium 2-ethyl hexanoate in acetone. The resulting suspension was filtered under suction and the wet cake was washed with acetone (440 ml) to provide the crude solid. The solid was further dried under vacuum at 40° C. to yield 40 g of (2S, 5R)-7-oxo-6-sulphooxy-2-[((3R)-piperidine-3-carbonyl)-hydrazinocarbonyl]-1,6-diaza-bicyclo[3.2.1]octane (I).

Analysis:
Mass: 392.2 (M+1); for Molecular formula of $C_{13}H_{21}N_5O_7S$ and Molecular Weight of 391.4;
Purity as determined by HPLC: 92.87%; and
Melting point as determined by DSC: 274° C.

Example 2

Synthesis of Pure (2S, 5R)-7-oxo-6-sulphooxy-2-[((3R)-piperidine-3-carbonyl)-hydrazinocarbonyl]-1,6-diaza-bicyclo[3.2.1]octane (I)

Step-1: Preparation of (2S, 5R)-6-hydroxy-7-oxo-2-[((3R)—N-Boc-piperidine-3-carbonyl)-hydrazinocarbonyl]-1,6-diaza-bicyclo[3.2.1]octane (III)

The procedure for the synthesis of (2S, 5R)-6-hydroxy-7-oxo-2-[((3R)—N-Boc-piperidine-3-carbonyl)-hydrazinocarbonyl]-1,6-diaza-bicyclo[3.2.1]octane (III) is same as given in Step-1 of Example 1.

Step-2: Preparation of tetrabutylammonium salt of (2S, 5R)-6-sulfooxy-7-oxo-2-[((3R)—N-Boc-piperidine-3-carbonyl)-hydrazinocarbonyl]-1,6-diaza-bicyclo[3.2.1] octane (IV)

A solution of (2S, 5R)-6-hydroxy-7-oxo-2-[((3R)—N-Boc-piperidine-3-carbonyl)-hydrazinocarbonyl]-1,6-diaza-bicyclo[3.2.1]octane (III) (106 g, 0.26 mol) in dichloromethane was charged with triethylamine (110 ml, 0.78 mol) under stirring to provide a clear solution. To this clear solution was added pyridine sulfur trioxide complex (82.5 g, 0.53 mol) under nitrogen atmosphere and stirred at temperature of about 30° C. for 2 hours. The reaction mixture was diluted with 0.5 N aqueous potassium dihydrogen phosphate solution (2100 ml) followed by ethyl acetate (2100 ml). The turbid solution was stirred for 15 minutes and then the layers were separated. The aqueous layer was washed with dichloromethane (530 ml) and then with ethyl acetate (1060 ml) respectively. Tetrabutyl ammonium sulfate (79 g, 0.23 mol) was added to the separated aqueous layer and stirred for 12 hours. The extraction of the product was done using dichloromethane as solvent (1150 ml×2). Aliquot of the organic layer was dried over sodium sulfate for purity check. Considering the purity of the product as obtained above, silica gel (530 g) was added to the dichloromethane layer and stirred for 1 hour. This was filtered and again silica was taken in dichloromethane (3200 ml) and stirred for 45 minutes and filtered. Combined dichloromethane layer was filtered through the celite bed again and washed with additional 200 ml dichloromethane. The solvent was removed to obtain 88 g of tetrabutylammonium salt of (2S, 5R)-6-sulfooxy-7-oxo-2-[((3R)—N-Boc-piperidine-3-carbonyl)-hydrazinocarbonyl]-1,6-diaza-bicyclo[3.2.1]octane (IV) as white foam.

Analysis:
Mass: 490.3 (M−1) as a free sulfonic acid; for Molecular Formula of $C_{18}H_{28}N_5O_9S.N(C_4H_9)_4$ and Molecular Weight of 733.0; and
Purity as determined by HPLC: 98.34%.

Step-3: Preparation of (2S, 5R)-7-oxo-6-sulphooxy-2-[((3R)-piperidine-3-carbonyl)-hydrazinocarbonyl]-1,6-diaza-bicyclo[3.2.1]octane (I)

The above obtained tetrabutylammonium salt of (2S, 5R)-6-sulfooxy-7-oxo-2-[((3R)—N-Boc-piperidine-3-carbonyl)-hydrazinocarbonyl]-1,6-diaza-bicyclo[3.2.1]octane (IV) having purity of more than 98% (88 g, 0.12 mol) was dissolved in dichloromethane (225 ml). The reaction mass was cooled to temperature of about −10° C. and to this trifluoroacetic acid (225 ml) was added slowly. The reaction mixture was stirred for 1 hour at about −10° C. The solvent was removed under high vacuum at temperature of about 30° C. The residue (280 g) was stirred with diethyl ether (1320 ml) for 1 hour. The precipitated solid was filtered and the cake was washed with fresh diethyl ether (440 ml). This process was repeated with fresh diethyl ether (1320 ml+440 ml). The obtained white solid was dried at about 30° C. and suspended in acetone (1320 ml). The pH of the suspension was adjusted to 6.5-7.0 using 10% solution of sodium 2-ethyl hexanoate in acetone. The resulting suspension was filtered under suction and the wet cake was washed with acetone (440 ml) to provide the crude solid. The solid was further dried under vacuum at 40° C. to yield 40 g of (2S, 5R)-7-oxo-6-sulphooxy-2-[((3R)-piperidine-3-carbonyl)-hydrazinocarbonyl]-1,6-diaza-bicyclo[3.2.1]octane (I).

Analysis:
Mass: 392.2 (M+1); for Molecular Formula of $C_{13}H_{21}N_5O_7S$ and Molecular Weight of 391.4; and
Purity as determined by HPLC: 98.7%.

Recovery of tetrabutylammonium salt of (2S, 5R)-6-sulfooxy-7-oxo-2-[((3R)—N-Boc-piperidine-3-carbonyl)-hydrazinocarbonyl]-1,6-diaza-bicyclo[3.2.1]octane (IV)

The silica recovered from the Step-2 was stirred with dichloromethane containing 2% methanol (2000 ml) for one hour. Silica was filtered, washed with additional same composition of solvents (500 ml). Combined dichloromethane was filtered through the celite bed and washed with same composition of solvents (200 ml), evaporated to afford 11 g of tetrabutylammonium salt of (2S, 5R)-6-sulfooxy-7-oxo-2-[((3R)-N-Boc-piperidine-3-carbonyl)-hydrazinocarbonyl]-1,6-diaza-bicyclo[3.2.1]octane (IV) as off white solid.

Repeating Step-3 with the above obtained tetrabutylammonium salt of (2S, 5R)-6-sulfooxy-7-oxo-2-[((3R)—N-Boc-piperidine-3-carbonyl)-hydrazinocarbonyl]-1,6-diaza-bicyclo[3.2.1]octane (IV) produced additional 7 g of compound of Formula (I).

Analysis:
Mass: 392.2 (M+1); for Molecular Formula of $C_{13}H_{21}N_5O_7S$ and Molecular Weight of 391.4;
Purity as determined by HPLC: 98.7%; and
Assay as determined by HPLC: 104% against reference standard of compound of Formula (I).

Example 3

Preparation of amorphous form of (2S, 5R)-7-oxo-6-sulphooxy-2-[((3R)-piperidine-3-carbonyl)-hydrazinocarbonyl]-1,6-diaza-bicyclo[3.2.1]octane (I)

Tetrabutylammonium salt of (2S, 5R)-6-sulfooxy-7-oxo-2-[((3R)—N-Boc-piperidine-3-carbonyl)-hydrazinocarbonyl]-1,6-diaza-bicyclo[3.2.1]octane (IV) (60 g, 0.081 mol), obtained in Step-2 of Example-2 was dissolved in dichloromethane (150 ml, 2.5 volume) to obtain a clear solution. Reaction mass was cooled to about −10° C. and to it trifluoroacetic acid (150 ml) was slowly added. The reaction mixture was stirred for 1 hour at about −10° C. The solvent was removed under high vacuum at about 30° C. Diethyl ether (600 ml×3) was added to the residue (184 g) and stirred for 15 minute every time. The solvent was decanted off and the residue was washed with acetonitrile (600 ml×3). This process was also repeated with dichloromethane (600 ml×3). The off white solid was isolated and dried under high vacuum at about 35° C. for 3 hour to obtain 33 g of amorphous form of (2S, 5R)-7-oxo-6-sulphooxy-2-[((3R)-piperidine-3-carbonyl)-hydrazinocarbonyl]-1,6-diaza-bicyclo[3.2.1]octane (I). The XRD is shown in FIG. 1.

Analysis:
Mass: 392.2 (M+1); for Molecular Formula of $C_{13}H_{21}N_5O_7S$ and Molecular Weight of 391.4;
HPLC purity: 92.26%; and
Melting point as determined by DSC: 210° C. (loss of moisture below 100° C.).

Example 4

Preparation of crystalline form of (2S, 5R)-7-oxo-6-sulpho-oxy-2-[((3R)-piperidine-3-carbonyl)-hydrazinocarbonyl]-1,6-diaza-bicyclo[3.2.1]octane (I)

The (2S, 5R)-7-oxo-6-sulphooxy-2-[((3R)-piperidine-3-carbonyl)-hydrazino carbonyl]-1,6-diaza-bicyclo[3.2.1]octane (I) obtained as white solid (40 g) in Step-3 of Example 2 was dissolved in demineralised water (40 ml) to obtain a clear solution. To this isopropyl alcohol (280 ml) was added under stirring at room temperature. The obtained turbid solution became sticky initially then slowly started to convert into white solid, stirring continued for about 17 hours at temperature of about 30° C. The precipitated solid was filtered and washed with water:isopropyl alcohol mixture (20 ml:140 ml). White solid was dried under high vacuum at temperature of about 45° C. for 5 hours to get 34 g of crystalline form of (2S, 5R)-7-oxo-6-sulphooxy-2-[((3R)-piperidine-3-carbonyl)-hydrazinocarbonyl]-1,6-diaza-bicyclo[3.2.1]octane (I).

Analysis:
Mass: 392.2 (M+1) for Molecular Formula of $C_{13}H_{21}N_5O_7S$ and Molecular Weight of 391.4;
Purity as determined by HPLC: 98.7%;

Assay as determined by HPLC: 104% against reference standard of compound of Formula (I); and Melting point as determined by DSC: 278° C. (9% loss of moisture at 143-152° C.).

X-ray powder diffraction pattern comprising a peak selected from the group consisting of 10.31 (±0.2), 10.59 (±0.2), 12.56 (±0.2), 13.84 (±0.2), 15.65 (±0.2), 18.19 (±0.2), 18.51 (±0.2), 20.38 (±0.2), 20.65 (±0.2), 24.30 (±0.2), 24.85 (±0.2) and 25.47 (±0.2) degrees 2 theta.

Typical X-ray analysis was performed as follows. Pass the test substance through sieve #100 BSS or gently grind it with a mortar and pestle. Place the test substance uniformly on a sample holder having cavity surface on one side, press the sample and cut into thin uniform film using a glass slide in such a way that the surface of the sample should be smooth and even. Record the X-ray diffractogram using the following instrument parameters.

Instrument: X-Ray Diffractometer
(PANalytical, Model X'Pert Pro MPD)
Target source: CuK(α)
Antiscattering slit (Incident beam): 1°
Programmable Divergent slit: 10 mm (fixed)
Anti-scattering slit (Diffracted beam): 5.5 mm
Step width: 0.02°
Voltage: 40 kV
Current: 40 mA
Time per step: 30 seconds
Scan range: 3 to 40°

The invention claimed is:

1. A process for preparation of a compound of Formula (I):

Formula (I)

comprising:
(a) hydrogenolysis of a compound of Formula (II) to obtain a compound of Formula (III);

Formula (II)

Formula (III)

(b) sulfonating the compound of Formula (III) to obtain a compound of Formula (IV);

Formula (IV)

(c) purifying the compound of Formula (IV) using a siliceous material; and
(d) deprotecting the compound of Formula (IV) obtained in step (c) to obtain the compound of Formula (I).

2. The process according to claim 1, wherein the siliceous material is a silica gel.

3. The process according to claim 1, wherein the compound of Formula (III) is obtained by hydrogenolysis of the compound of Formula (II) in presence of a transition metal catalyst and a hydrogen source.

4. The process according to claim 3, wherein the transition metal catalyst is a palladium on carbon catalyst and the hydrogen source is a hydrogen gas.

5. The process according to claim 1, wherein the compound of Formula (IV) is obtained by sulfonation of the compound of Formula (III) with a pyridine-sulfur trioxide complex, followed by treatment with tetra butyl ammonium acetate.

6. The process according to claim 1, wherein the compound of Formula (IV) is converted into the compound of Formula (I) by reacting with trifluoroacetic acid.

7. The process according to claim 1, wherein the compound of Formula (I):

Formula (I)

obtained is having a purity of more than about 98% as determined by HPLC.

8. A pharmaceutical composition comprising a compound of Formula (I):

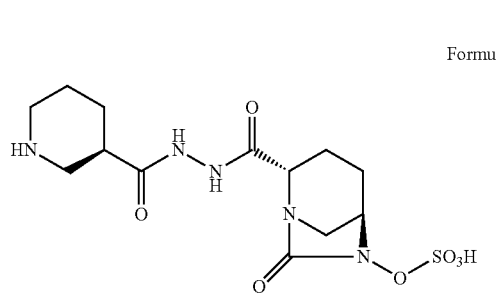

Formula (I)

in a crystalline form; wherein said crystalline form having an X-ray powder diffraction pattern comprising a peak selected from the group consisting of 10.31 (±0.2), 10.59 (±0.2), 12.56 (±0.2), 13.84 (±0.2), 15.65 (±0.2), 18.19 (±0.2), 18.51 (±0.2), 20.38 (±0.2), 20.65 (±0.2), 24.30 (±0.2), 24.85 (±0.2) and 25.47 (±0.2) degrees 2 theta.

9. A pharmaceutical composition comprising a compound of Formula (I):

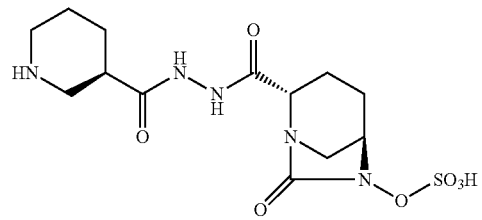

Formula (I)

in a crystalline form; said crystalline form having an X-ray powder diffraction pattern comprising a peak selected from the group consisting of 10.31 (±0.2), 12.56 (±0.2), 13.84 (±0.2), 15.65 (±0.2), 18.19 (±0.2), 18.51 (±0.2), 20.38 (±0.2) and 24.30 (±0.2) degrees 2 theta.

10. The pharmaceutical composition according to claim 8, wherein the pharmaceutical composition further comprising one or more pharmaceutically acceptable inactive ingredients.

11. The pharmaceutical composition according to claim 9, wherein the pharmaceutical composition further comprising one or more pharmaceutically acceptable inactive ingredients.

* * * * *